(12) United States Patent
Clarke

(10) Patent No.: US 8,480,727 B2
(45) Date of Patent: Jul. 9, 2013

(54) ENDOVASCULAR IMPLANT HAVING AN INTEGRAL GRAFT COMPONENT AND METHOD OF MANUFACTURE

(75) Inventor: Gerry Clarke, Moycullen (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 13/613,161

(22) Filed: Sep. 13, 2012

(65) Prior Publication Data
US 2013/0013054 A1 Jan. 10, 2013

Related U.S. Application Data

(62) Division of application No. 12/425,653, filed on Apr. 17, 2009, now abandoned.

(51) Int. Cl.
| | |
|---|---|
| *A61F 2/06* | (2006.01) |
| *B29C 45/14* | (2006.01) |
| *B29C 35/00* | (2006.01) |
| *B29C 45/00* | (2006.01) |
| *A23P 1/00* | (2006.01) |
| *B29B 11/06* | (2006.01) |

(52) U.S. Cl.
USPC ................ 623/1.13; 264/279; 425/542

(58) Field of Classification Search
USPC ................. 623/1.1–1.22; 264/279; 425/542
See application file for complete search history.

(56) References Cited

U.S. PATENT DOCUMENTS

| | | | |
|---|---|---|---|
| 4,550,447 A | 11/1985 | Seiler et al. | |
| 4,733,665 A | 3/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,421,955 A | 6/1995 | Lau | |
| 5,599,352 A | 2/1997 | Dinh et al. | |
| 5,609,624 A | 3/1997 | Kalis | |
| 5,776,161 A | 7/1998 | Globerman | |
| 5,897,911 A | 4/1999 | Loeffler | |
| 5,935,162 A | 8/1999 | Dang | |
| 6,090,127 A | 7/2000 | Globerman | |
| 6,113,627 A | 9/2000 | Jang | |
| 6,143,022 A | 11/2000 | Shull et al. | |
| 6,488,701 B1 * | 12/2002 | Nolting et al. ............... | 623/1.13 |
| 6,514,063 B2 | 2/2003 | Acciai et al. | |
| 6,537,310 B1 * | 3/2003 | Palmaz et al. ................ | 623/1.13 |
| 6,574,851 B1 | 6/2003 | Mirizzi | |
| 6,663,661 B2 | 12/2003 | Boneau | |

(Continued)

FOREIGN PATENT DOCUMENTS

| | | |
|---|---|---|
| FR | 2768920 | 4/1999 |
| WO | WO2008/115678 | 9/2008 |

*Primary Examiner* — Gary Jackson
*Assistant Examiner* — Michael Mendoza

(57) ABSTRACT

A covered stent including an endovascular implant having a polymeric stent structure with an integrally formed membrane-like graft component, also referred to as a stent-graft, and methods of manufacturing the one-piece stent-graft by an injection molding process. A molding system for creating the polymeric stent structure is injected with a melt stream of moldable material that is forced between a parting line of the molding system to create a thin, flexible membrane-like structure within the open areas or interstitial spaces of the molded stent structure. The stent-graft so created is a one-piece, unified structure molded from a polymeric material in a single manufacturing step.

10 Claims, 8 Drawing Sheets

U.S. PATENT DOCUMENTS

| | | |
|---|---|---|
| 6,730,116 B1 | 5/2004 | Wolinsky et al. |
| 6,849,085 B2 * | 2/2005 | Marton ............... 623/1.13 |
| 6,866,805 B2 | 3/2005 | Hong et al. |
| 2003/0028240 A1 | 2/2003 | Nolting et al. |
| 2003/0074053 A1 | 4/2003 | Palmaz et al. |
| 2003/0130718 A1 | 7/2003 | Palmas et al. |
| 2004/0111111 A1 | 6/2004 | Lin |
| 2005/0273154 A1 | 12/2005 | Colone |
| 2006/0036308 A1 * | 2/2006 | Goshgarian ............ 623/1.11 |
| 2006/0129228 A1 | 6/2006 | Golesworthy et al. |
| 2006/0136041 A1 | 6/2006 | Schmidt et al. |
| 2006/0287715 A1 | 12/2006 | Atladottir et al. |
| 2008/0001330 A1 | 1/2008 | Huang et al. |
| 2008/0234831 A1 | 9/2008 | Clarke et al. |
| 2008/0262596 A1 | 10/2008 | Xiao |

* cited by examiner

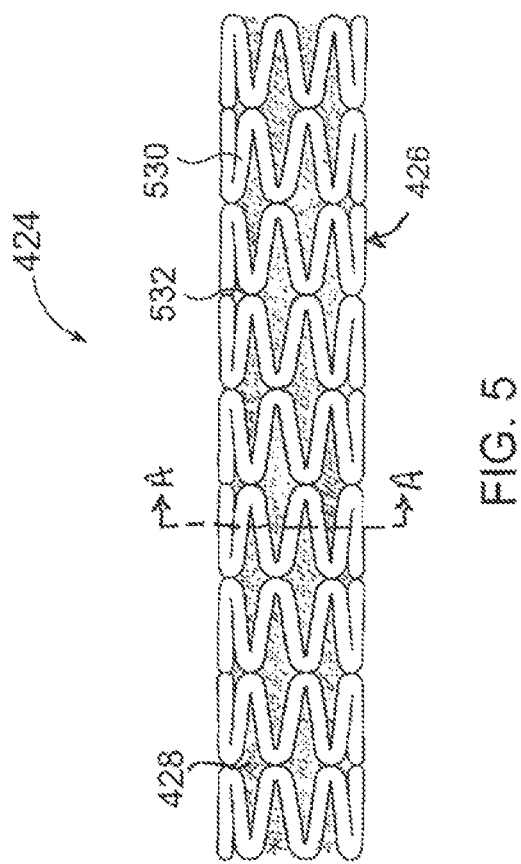

ENDOVASCULAR IMPLANT HAVING AN INTEGRAL GRAFT COMPONENT AND METHOD OF MANUFACTURE

RELATED APPLICATIONS

This application is a Division of and claims the benefit of U.S. patent application Ser. No. 12/425,653 filed Apr. 17, 2009. The disclosures of which are herein incorporated by reference in their entirety.

FIELD OF THE INVENTION

The invention relates generally to endoluminal medical devices having a graft component, and more particularly to an endovascular implant having an integral graft component and methods of manufacture thereof.

BACKGROUND

Prostheses for implantation in blood vessels or other similar organs of the living body are, in general, well known in the medical art. For example, prosthetic vascular grafts constructed of biocompatible materials, such as Dacron material or expanded, porous polytetrafluoroethylene (ePTFE) tubing, have been employed to replace or bypass damaged or occluded natural blood vessels. In general, endovascularly delivered grafts typically include a graft anchoring component that operates to hold the tubular graft in its intended position within the blood vessel. Most commonly, the graft anchoring component is one or more radially compressible stents that are radially expanded in vivo to anchor the tubular graft to the wall of a blood vessel or anatomical conduit. Thus, endovascular grafts are typically held in place by mechanical engagement and friction due to the apposition forces provided by the expandable stents.

In general, rather than performing an open surgical procedure to implant a graft that may be traumatic and invasive, endovascular grafts or stent-grafts are preferably deployed through a less invasive intraluminal delivery. These stent-grafts may include either self-expanding or balloon-expandable stent structures with a tubular graft component attached to the stent structure. The stent-graft can be reduced in diameter, by crimping onto a balloon catheter or by being contained within a sheath component of a delivery catheter, and advanced through the venous or arterial vasculature. More particularly, a lumen of the vasculature is accessed at a convenient and low trauma entry point, and the compressed or crimped stent-graft is routed through the vasculature to the site where the prosthesis is to be deployed. Once the stent-graft is positioned at a treatment site, the stent structure may be radially expanded or allowed to radially expand so that at least a portion of it contacts and substantially conforms to a portion of the surrounding interior wall of the lumen, e.g., the blood vessel wall or in another application an anatomical conduit, to hold the graft component firmly in place.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular stent-graft may be placed within the blood vessel to span the aneurysm to create an artificial flow conduit through the aneurysm, thereby reducing if not nearly eliminating the exertion of blood pressure on the aneurysm.

Many current endovascular stent-grafts are complex and expensive to manufacture, often requiring numerous processing steps to separately form the stent structure and graft component and then additional processing steps to attach the graft component to the stent structure, which in some instances is rather labor intensive when the attachment is accomplished by suturing, i.e., sewing the graft component to the stent structure. Adding a graft component to the stent structure also increases the challenges of delivering the endovascular stent-graft via a catheter-based delivery system by increasing the crossing profile, or diameter, of the interventional device, and/or by decreasing the flexibility of the interventional device.

Thus, those of skill in the art seek improvements in providing an endovascular stent-graft having a sufficiently small crossing profile that is sufficiently flexible for readily tracking through the vasculature. In addition, a need remains in the art for a simplified manufacturing process for creating such a stent-graft. Embodiments of an endovascular implant described herein have an integral graft component that is manufactured in a single processing step.

BRIEF SUMMARY OF THE INVENTION

An endovascular implant has a polymeric stent structure with an integrally formed membrane-like graft component, also referred to as a stent-graft. Methods of manufacturing the one-piece stent-graft by an injection molding process including using a molding system for creating the polymeric stent structure which is injected with a melt stream of moldable material that is forced to flow between a parting line of the molding system to create a thin, flexible membrane-like structure within the open areas or interstitial spaces of the molded stent structure. A stent-graft so created is a one-piece unified structure molded using a polymeric material in a single manufacturing step.

BRIEF DESCRIPTION OF DRAWINGS

The foregoing and other features and advantages of embodiments according to the present invention will be apparent from the following description as illustrated in the accompanying drawings. The accompanying drawings, which are incorporated herein and form a part of the specification, further serve to explain the principles of the embodiments and to enable a person skilled in the pertinent art to make and use the described embodiments herein. The drawings are not to scale.

FIG. 5 is a plan view of a polymeric stent-graft having an integral graft component made in accordance with an embodiment hereof.

DETAILED DESCRIPTION

Specific embodiments are now described with reference to the figures, wherein like reference numbers indicate identical or functionally similar elements. A polymeric endovascular stent-graft and a method of making the same are described.

The following detailed description is merely exemplary in nature. Although the description is in the context of an endovascular stent-graft for treatment of a blood vessel, embodiments hereof may also be used in any other body passageway where they are deemed useful.

Figure 1:
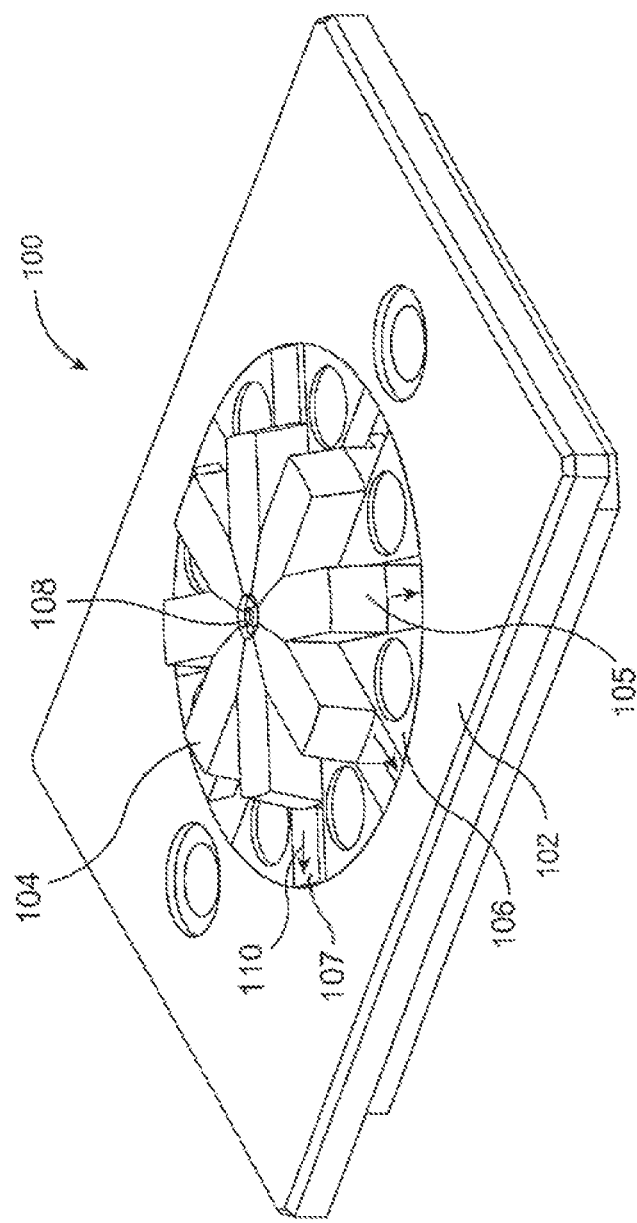
FIG. 1 is a perspective view of an injection molding system for use in molding an endovascular stent-graft having an integral graft component in accordance with an embodiment hereof.
Figure 3:
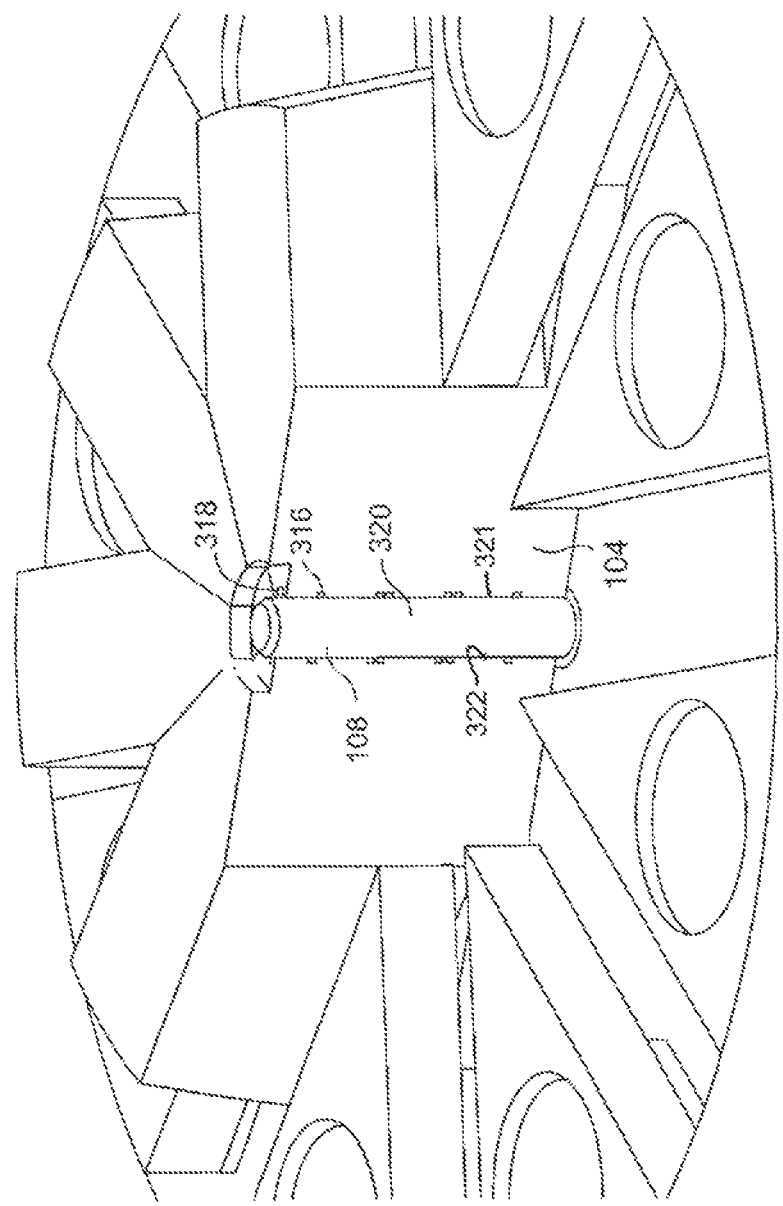
FIG. 3 is a partial cut-away view of the injection molding system of FIG. 1 in a mold closed position.
Figure 4:
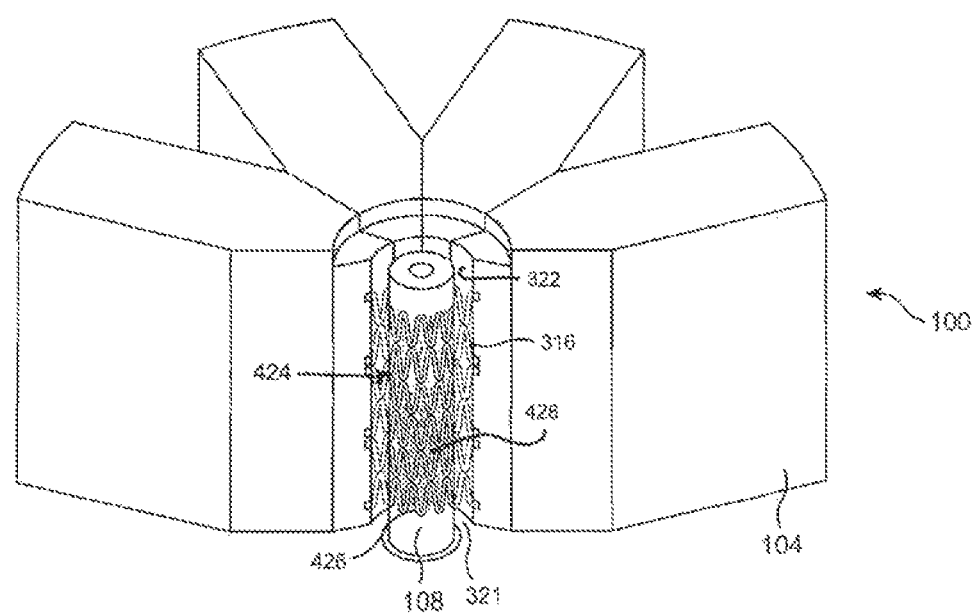
FIG. 4 is a close up partial cut-away view of a portion of the injection molding system of FIG. 1 in a mold open position.

FIG. 1 is a perspective view of a molding system 100 used to form a unitary, one-piece stent-graft. Molding system 100 includes a lower mold plate 102, slidable cavity plates 104, slide guide blocks 106, and a centrally-located mold core pin 108. In FIGS. 1 and 3 (FIG. 3 is a partial cut-away view of molding system 100), molding system 100 is shown with slidable cavity plates 104 in a mold closed position to cooperate with mold core pin 108 to form a mold cavity 316 therebetween, as discussed in more detail below. Slidable cavity plates 104 slide within radial tracks 107, which are defined by adjacent slide guide blocks 106, and are moved to a mold open position as shown in FIG. 4 by being slid away from mold core pin 108 in the direction shown by arrows 110 in FIG. 1. Although eight cavity plates 104 and guide blocks 106 are shown in the embodiment of FIG. 1, it is understood by one of ordinary skill in the art of mold design that more or fewer cavity plates and guide blocks of alternate shapes and sizes could be used.

Figure 2:
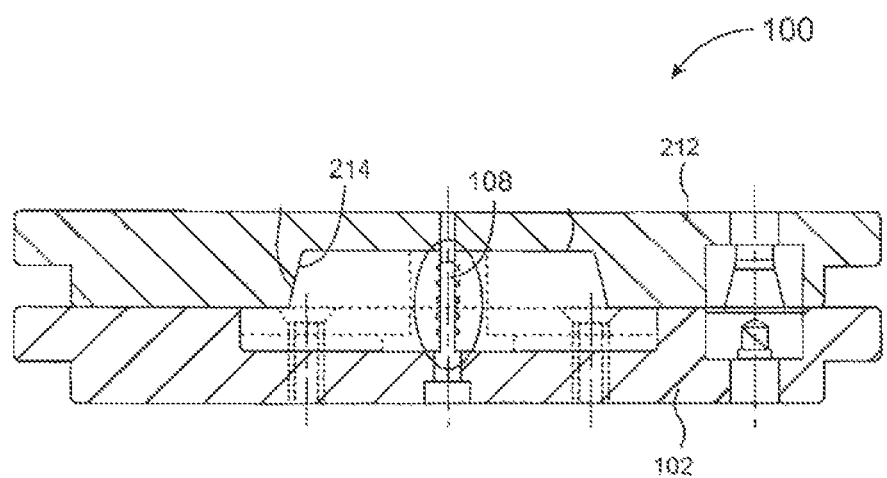
FIG. 2 is a partial sectional view of the injection molding system of FIG. 1 within upper and lower mold plates.

FIG. 2 is a partial sectional view of molding system 100 of FIG. 1 with an upper mold plate 212 secured to lower mold plate 102, such as by bolting, clamping or other attachment mechanisms known in the art. Upper mold plate 212 includes a recess 214 that is shaped to surround and hold slidable cavity plates 104 in the closed position. Recess 214 of upper mold plate 212 includes slanted side walls that are shaped to correspond to and engage with slanted exterior walls 105 of cavity plates 104 to aid in closing molding system 100. A more detailed description of the operation of the slidable cavity plates of molding system 100 may be found with reference to injection molding system (10) of U.S. Pat. Appl. Pub. No. 2008/0234831 to Clarke et al., which is incorporated by reference herein in its entirety.

The process for forming an endovascular stent-graft 424 having a molded stent structure or framework 426 with a thin, integrally formed membrane-like structure or graft component 428 will be described with reference to molding system 100 shown in FIGS. 3 and 4. Mold cavity 316 for molding stent structure 426, as described in the Clarke et al. publication incorporated by reference above, is defined by a series of recessed grooves that are disposed within surfaces 322 of cavity plates 104 and surface 320 of mold core pin 108, which forms an interior surface of molded stent structure 426. Cavity plate surfaces 322 and mold core pin surface 320 are opposing curved mating surfaces that meet along a parting line 321 of molding system 100, and may also be referred to as parting surfaces of the molding system. Mold cavity 316 is designed to create molded stent structure 426 in an expanded or deployed configuration, i.e., with an outer diameter that would be in apposition with a wall of a body vessel in vivo.

To form stent-graft 424 having integrally formed graft component 428, a melt stream of a moldable polymeric material is injected into closed mold cavity 316 through one or more mold gate(s) 318 to fill mold cavity 316 with melt. After mold cavity 316 is filled with melt, such that the recessed grooves that form the shape of molded stent structure 426 are full, the melt stream is briefly continued to force the melt stream to seep between parting surfaces 320, 322 thereby covering the interstitial areas of molded stent structure 426 by forming a very thin membrane-like graft component 428 therebetween. In order to assure a proper thickness of the melt stream between parting surfaces 320, 322 to form graft component 428, parting surfaces 320, 322 may be physically limited from complete closure by hard stops or pins of, for instance, 0.0005 inch to 0.001 inch in length extending from one of parting surfaces 320, 322 to rest against the other of parting surfaces 320, 322 in the mold closed position to create a slight gap that may be filled with the overflow or excess melt from mold cavity 316 and may then form a very thin integral graft component 428.

In another embodiment to facilitate a proper thickness of the melt stream between parting surfaces 320, 322 to form graft component 428, a slight tolerance of, for e.g., approximately 0.0005 inch to 0.001 inch may be maintained between parting surface 320 of mold core pin 108 and mating parting surfaces 322 of cavity plates 104 such that a slight gap is created that may be filled with the overflow or excess melt from mold cavity 316 and may then form a very thin integral graft component 428. In another embodiment, a pressure, temperature, and/or viscosity of the melt stream may be manipulated to ease forcing the melt stream between parting surfaces 320, 322 of molding system 100. Stent-graft 424 having integral graft component 428 is cooled and then removed from molding system 100 by sliding cavity plates 104 to a mold open position. In this manner, a one-piece stent-graft may be formed by injection molding in essentially a single manufacturing step.

"Flash" or "flashing" as used conventionally means excess material attached to a molded product that is typically caused by leakage of the material between the two surfaces, i.e., along a parting line, of a mold and is commonly considered a quality defect. Thus, one of ordinary skill in the art of injection molding attempts to limit or eliminate flashing within the parting line of the mold and/or to remove flash material from a finished product. Accordingly, it is understood by one of ordinary skill in the art of injection molding that intentionally forcing the melt stream between parting surfaces of a molding system as disclosed in the preceding method of manufacturing a one-piece stent-graft according to embodiments hereof would not be considered "flash" or "flashing".

Figure 3A:
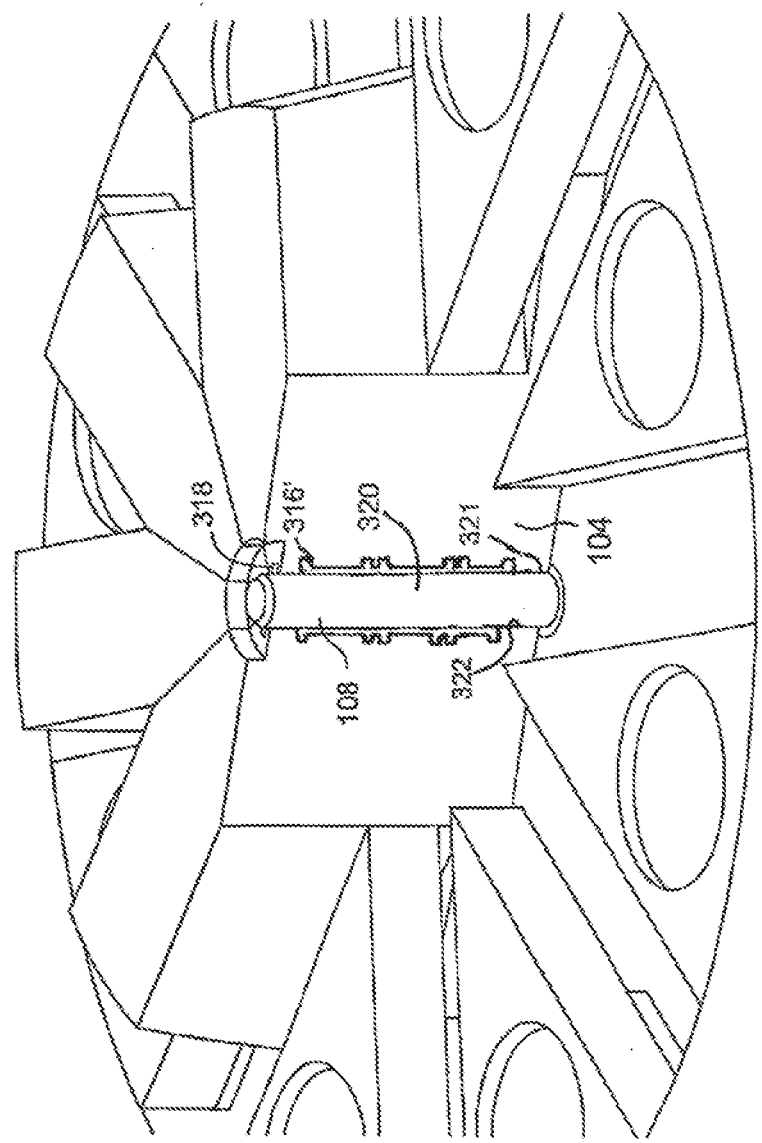
FIG. 3A is a partial cut-away view of another embodiment of the injection molding system of FIG. 1 in a mold closed position

In another embodiment shown in FIG. 3A, mold cavity 316' in parting surfaces 322 is formed to include a cavity portion for defining a graft component between a stent structure. The graft component cavity portion would provide for molding a thin membrane-like graft component with a thickness of 0.0005 inch to 0.001 inch between the stent structure in a single manufacturing step.

Figure 5A:
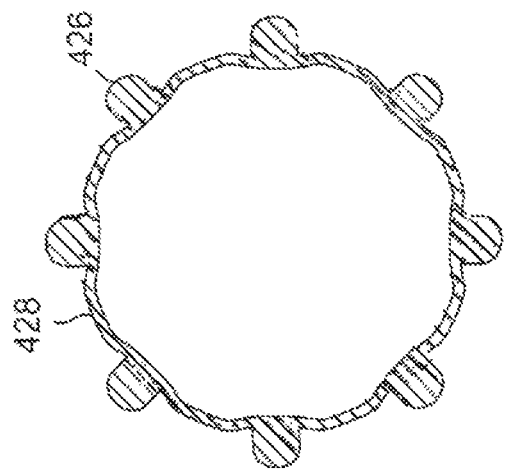
FIG. 5A is a cross-sectional view of the stent-graft of FIG. 5 taken along line A-A.

FIG. 5 is a side view of a polymeric stent-graft 424 having integral graft component 428 made in accordance with methods hereof, with FIG. 5A being a cross-section of stent-graft 424 taken along line A-A of FIG. 5. Molded stent structure 426 includes frame members that may be described as struts 530 and crowns 532, which are bends that connect struts 530. Struts 530 and crowns 532 may also be referred to as forming a sinusoidal ring, a series of which form molded stent structure 426. In one embodiment, stent structure 426 may be "self-expanding", which as used herein means that stent structure 426 has a mechanical shape memory to return to an expanded or deployed configuration, such as for example, when a shape memory polymer as disclosed in U.S. Pat. Appl. Pub. No. 2004/0111111 to Lin, which is incorporated by reference herein in its entirety, is used to form stent-graft 424. In another embodiment, stent structure 426 may be balloon-expandable. Graft component 428 is a membrane-like structure that covers or otherwise extends within the interstices or small open spaces defined between adjacent frame members, such as adjacent struts 530, and in embodiments hereof is substantially impermeable to form a longitudinally extending lumen through stent-graft 424 that may be used to direct blood flow when stent-graft 424 is deployed within a body vessel. Since stent-graft 424 is molded in an expanded configuration and the molded graft component is very thin, such as ≦0.001 inch, the graft component is able to fold or pucker onto itself when one-piece stent-graft 424 is crimped on or otherwise compressed within a delivery device. In the embodiment of FIGS. 5 and 5A, the membrane-like graft component 424 may be described as being substantially formed at an interior side of stent structure 426 and/or as forming an interior surface of stent-graft 424.

Figure 6:
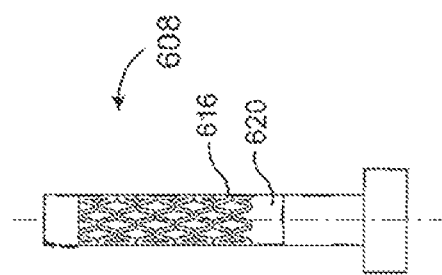
FIG. 6 is a side view of an alternate embodiment of a mold core pin.
Figure 7:
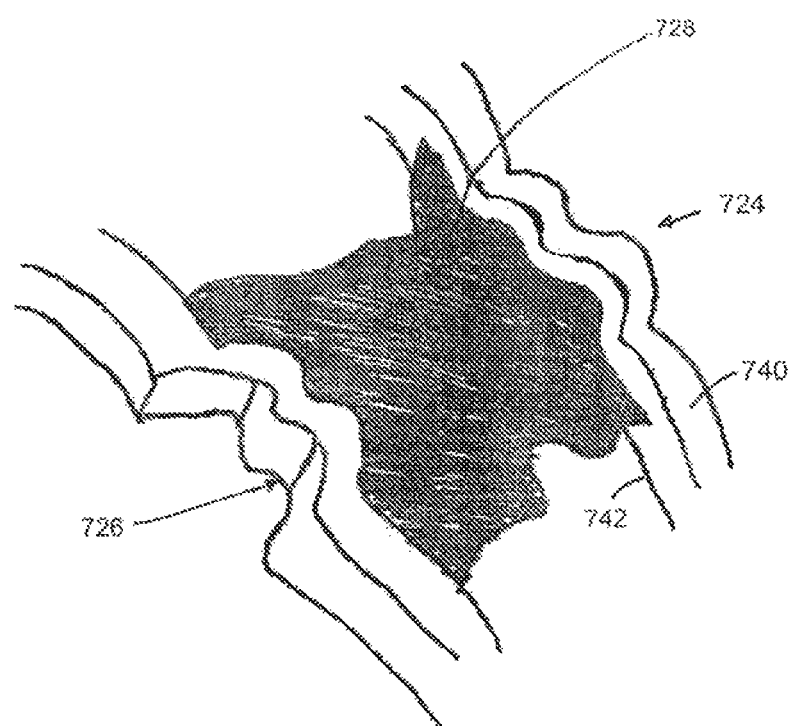
FIG. 7 is a perspective view of a portion of an endovascular stent-graft having an integral graft component in accordance with another embodiment hereof.

In another embodiment, shown in FIG. 6, mold core pin 608 may have corresponding grooves formed in a parting or mating surface 620 thereof to define a mold cavity 616 that forms an inner portion or a first half of a molded stent framework when aligned with corresponding grooves in parting surfaces of slidable cavity plates (not shown) that form an outer portion or a second half of the molded stent framework. A mold cavity so constructed may then be used to produce a stent-graft with an integral graft component by injection molding, as described with reference to the preceding embodiments. However, such a mold cavity configuration with parting surfaces at substantially a midpoint of the width of the molded stent framework will produce a stent-graft 724, a portion of which is illustrated in FIG. 7, where the integral graft component 728 is positioned substantially midway between exterior and interior surfaces 740, 742 of the molded stent structure 726. In such an embodiment, integrally formed graft component 728 may be considered to be comprised of a plurality of separate graft component segments.

In another embodiment, the grooves of mold core pin (e.g., 608) formed in the parting surface (e.g., 620) thereof define a mold cavity (e.g., 616) that aligns with curved planar parting surfaces of slidable cavity plates (not shown) in a mold closed position. As such, the mold cavity (e.g., 616) forms substantially the entire molded stent framework with the curved planar surface of the slidable cavity plates defining an exterior surface of the molded stent framework. The mold cavity (e.g., 616) so formed may then be used to produce a stent-graft with an integral graft component by injection molding, as described with reference to the preceding embodiment, wherein the membrane-like graft component is substantially formed at an exterior side of the stent framework to substantially form an exterior surface of the one-piece stent-graft.

The polymeric material used to make stent-graft 424 may be any polymer suitable for use in a human body and for injection molding applications. Examples of polymers include but are not limited to, polyoxymethylene, such as DELRIN 100TL NC010 produced by DuPont of Wilmington, Del., poly-a-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO), polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

It will be appreciated by those of ordinary skill in the art that molded stent structure 426 of FIG. 5 is merely an exemplary stent structure and that the molded stent structure may take various forms in accordance with embodiments hereof. Some examples of stent frameworks that may be manufactured into stent-grafts by injection molding methods in accordance with embodiments hereof are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, U.S. Pat. No. 6,730,116 to Wolinsky et al. and U.S. Pat. Appl. Pub. No. 2008/0234800 to Clarke, each of which is incorporated by reference herein in its entirety.

While various embodiments have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of manufacturing a one-piece stent-graft comprising:
   injecting a melt stream of moldable polymeric material into a mold cavity of a molding system, wherein the mold cavity forms a tubular stent framework having interstitial spaces;
   filling the mold cavity with the melt until the mold cavity overflows and the melt flows between parting surfaces of the molding system; and
   allowing the melt to cover the parting surfaces such that a molded tubular stent framework formed thereby has an integral thin membrane-like structure molded within the interstitial spaces thereof by the melt which has flowed between the parting surfaces.

2. The method of claim 1, wherein the integral thin membrane-like structure has a thickness of approximately 0.0005 inch to 0.001 inch.

3. The method of claim 1, wherein a gap of approximately 0.0005 inch is maintained between the parting surfaces of the molding system such that the integral thin membrane-like structure has a thickness of approximately 0.001 inch.

4. The method of claim 1, wherein the moldable polymeric material is polyoxymethylene.

5. The method of claim 1, wherein the mold cavity has a first portion formed within a first parting surface of the molding system and a second portion formed within a second parting surface of the molding system such that the integral thin membrane-like structure is molded within the interstitial spaces substantially midway between exterior and interior surfaces of the molded tubular stent framework.

6. The method of claim 5, wherein the first portion of the mold cavity are grooves formed in the first parting surface and the second portion of the mold cavity are grooves formed in the second parting surface that align with the grooves formed in the first parting surface to mold the tubular stent framework.

7. The method of claim 1, wherein the mold cavity is formed within surfaces of a series of cavity plates that together form one of the parting surfaces of the molding system.

8. The method of claim 7, wherein a surface of a mold core pin forms the other of the parting surfaces of the molding system.

9. The method of claim 8, wherein the cavity plate surfaces and the mold core pin surface are opposing curved surfaces.

10. The method of claim 8, wherein the integral thin membrane-like structure is molded within the interstitial spaces substantially along an interior side of the molded tubular stent framework so as to form an interior surface of the stent-graft.

* * * * *